(12) United States Patent
Cheng et al.

(10) Patent No.: US 12,031,984 B2
(45) Date of Patent: Jul. 9, 2024

(54) DETECTION DEVICE USING LATERAL FLOW STRIP FOR DETECTION AND DETECTION METHOD THEREOF

(71) Applicant: CHINA AGRICULTURAL UNIVERSITY, Beijing (CN)

(72) Inventors: Nan Cheng, Beijing (CN); Xiaoyun He, Beijing (CN); Wentao Xu, Beijing (CN); Kunlun Huang, Beijing (CN); Yunbo Luo, Beijing (CN); Qian Zhang, Beijing (CN); Qingliang Liu, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 343 days.

(21) Appl. No.: 17/511,975

(22) Filed: Oct. 27, 2021

(65) Prior Publication Data

US 2023/0075293 A1 Mar. 9, 2023

(30) Foreign Application Priority Data

Sep. 6, 2021 (CN) .......................... 202111035917.1

(51) Int. Cl.
*G01N 33/543* (2006.01)
*G01N 35/10* (2006.01)

(52) U.S. Cl.
CPC . *G01N 33/54388* (2021.08); *G01N 33/54306* (2013.01); *G01N 2035/1088* (2013.01)

(58) Field of Classification Search
CPC ....... G01N 33/54388; G01N 33/54306; G01N 2035/0444; G01N 35/025; C12Q 1/6844; B01F 27/40; B01F 27/41; B01F 27/411; B01F 27/412; B01F 27/42; B01F 27/421; B01F 27/422
USPC ....... 422/400, 401, 420, 421, 425, 426, 430; 435/287.7, 287.9, 970, 805, 810, 169, 435/170, 514, 518, 530
See application file for complete search history.

(56) References Cited

U.S. PATENT DOCUMENTS

2004/0191121 A1 * 9/2004 Tomasso ................ G01N 35/04
422/63

FOREIGN PATENT DOCUMENTS

| CN | 109669037 A | * | 4/2019 | ....... G01N 33/54313 |
|---|---|---|---|---|
| CN | 109897910 A | | 6/2019 | |
| CN | 109917132 A | | 6/2019 | |

* cited by examiner

*Primary Examiner* — Christopher L Chin
*Assistant Examiner* — Christina Lusi
(74) *Attorney, Agent, or Firm* — Ohlandt, Greeley and Perle, LLP

(57) ABSTRACT

A detection device using a lateral flow strip for detection and a detection method thereof are provided, which relates to the technical field of a detection device using a lateral flow strip. An upper rotor, a middle rotor and a lower rotor are respectively provided with upper paddle(s), middle paddle(s) and lower paddle(s) along respective circumferential directions. Each upper paddle is provided with a test tube with openings at both ends thereof for placing the lateral flow strip. The middle paddle blocks a bottom one of the openings of the test tube. Each lower paddle is provided with a sample tube for placing sample solution. The bottom opening of the test tube is opposite to a top opening of the sample tube up and down.

15 Claims, 4 Drawing Sheets

DETECTION DEVICE USING LATERAL FLOW STRIP FOR DETECTION AND DETECTION METHOD THEREOF

CROSS REFERENCE TO RELATED APPLICATION

This patent application claims the benefit and priority of Chinese Patent Application No. 202111035917.1 filed on Sep. 6, 2021, the disclosure of which is incorporated by reference herein in its entirety as part of the present application.

TECHNICAL FIELD

The present disclosure relates to the technical field of a detection device using a lateral flow strip, and in particular, to a detection device using a lateral flow strip for detection and a detection method thereof.

BACKGROUND ART

A lateral flow strip (LFS) is low in detection cost, and thus there is no need for expensive and professional instruments and devices, which is simple in detection process, portable, and easy to operate. Furthermore, detection results of the LFS are visual, and the analysis time is short. So, the LFS plays an important role in on-site detection. At present, the lateral flow strip has been widely used in food safety detection, biomedicine, environmental monitoring and other fields. In the process of LFS detection, there is no special detection device at present, whereas the existing devices in the laboratory are usually used for detection, and that some steps of constant temperature nucleic-acid-amplification or constant temperature incubation are usually involved. However, at present, the constant temperature reaction steps and the LFS detection steps are mostly separated, so the detection device and the detection steps are complex, and the detection efficiency is low. For example, in the patent application documents with Application No. "201910230115.2" entitled "METHOD FOR RAPIDLY AND ACCURATELY DETECTING FUSARIUM OXYSPORUM USING RPA-LATERAL FLOW STRIP TECHNOLOGY", and Application No. "201910221549.6" entitled "PRIMER PAIR OF HPV 16 AND HPV 18 GENOTYPES, DUAL LATERAL FLOW STRIP AND DETECTION METHOD", the sample solution to be detected is firstly amplified, and then the detection is performed by using the lateral flow strip. When using lateral flow strips for detection, the common method in this field is to absorb partially the liquid to be detected by a dropper, and then drop the liquid on an absorption pad of the lateral flow strip. So, the process requires equipment such as pipettes or droppers, but also the lateral flow strips are easy to be polluted during this process, which affects the detection accuracy.

Therefore, it is an urgent technical problem to provide a special detection device using a lateral flow strip for detection to improve the detection efficiency and ensure the detection accuracy.

SUMMARY

The purpose of the present disclosure is to provide a detection device using a lateral flow strip for detection and a detection method thereof, so as to solve the problems existing in the prior art, improve the integration level of the detection device and improve the detection efficiency at the same time.

In order to achieve the above purpose, the present disclosure provides the following scheme. A detection device using a lateral flow strip for detection is provided, which includes an upper rotor, a middle rotor and a lower rotor from top to bottom which are coaxial and rotatable relatively, wherein the upper rotor, the middle rotor and the lower rotor are respectively provided with at least one upper paddle, at least one middle paddle and at least one lower paddle along respective circumferential directions; each of the at least one upper paddle is provided with a test tube with openings at two ends thereof, and the test tube is configured for placing the lateral flow strip; a bottom one of the openings of the test tube is used for enabling the lateral flow strip to fall out of the test tube; a corresponding one of the at least one middle paddle blocks the bottom one of the openings of the test tube; the at least one lower paddle is provided with at least one sample tube for placing sample solution in one-to-one correspondence; and the bottom one of the openings of the test tube is opposite to a top opening of a corresponding one of the at least one sample tube up and down.

Preferably, the at least one middle paddle is provided with a middle stirring block for stirring the at least one upper paddle to rotate synchronously and unidirectionally.

Preferably, the at least one middle paddle is further provided with a stirring lever for applying force to stir the at least one middle paddle to rotate.

Preferably, the middle stirring block and the stirring lever are located at two sides of a same middle paddle of the at least one middle paddle respectively, and the two sides are in a horizontal direction of the same middle paddle.

Preferably, one upper paddle of the at least one upper paddle is provided with an upper stirring block for stirring the at least one middle paddle to rotate synchronously and unidirectionally, and the upper stirring block is located at one side of the one upper paddle, the one side is in a horizontal direction of the one upper paddle, and the upper stirring block and the middle stirring block are at different sides.

Preferably, a bottom end of the upper stirring block is lower than a lower surface of a corresponding one of the at least one middle paddle.

Preferably, the at least one upper paddle, the at least one middle paddle and the at least one lower paddle are stacked, each of the at least one upper paddle is provided with an upper through hole, a bottom end of the test tube is fixed at the upper through hole, each of the at least one lower paddle is provided with a lower through hole, a top of a corresponding one of the at least one sample tube is fixed at the lower through hole, the upper through hole and the lower through hole are directly opposite to each other up and down. Preferably, the lower through hole is further provided with a vent hole for circulating air inside and outside a corresponding one of the at least one sample tube.

Preferably, the at least one upper paddle, the at least one middle paddle and the at least one lower paddle have same cross-sectional shapes, and are each provided with three paddles.

Preferably, the detection device further comprises a water tank for heating the at least one sample tube in a water bath manner, a support column is fixed in the water tank, the upper rotor, the middle rotor and the lower rotor are all fixed on the support column, and the at least one sample tube is located in the water tank.

A detection method using a lateral flow strip for detection is provided, the detection method is carried out by a detection device including at least one upper paddle, at least one middle paddle and at least one lower paddle, and the detection method includes: stacking and aligning the at least one upper paddle, the at least one middle paddle and the at least one lower paddle, and placing the lateral flow strip in a test tube on each of the at least one upper paddle; stirring the at least one middle paddle to rotate forward through a stirring lever of the at least one middle paddle, enabling the at least one upper paddle to rotate synchronously under driving of a middle stirring block of the at least one middle paddle, exposing a lower through hole of each of the at least one lower paddle after the at least one middle paddle rotates, and adding sample solution into at least one sample tube on the at least one lower paddle; stirring the at least one upper paddle reversely after the sample solution is added, and enabling the at least one middle paddle to rotate synchronously under driving of an upper stirring block of the at least one upper paddle, such that each of the at least one middle paddle is re-located above a corresponding one of the at least one lower paddle; adding warm water at a predetermined temperature into a water tank of the detection device to heat the sample solution in a water bath manner, wherein the warm water has a higher liquid level than the sample solution; rotating the at least one middle paddle forward after heating for predetermined time, and adding running buffer solution to the at least one sample tube; reversely rotating the at least one upper paddle, such that each of the at least one middle paddle is located right above a corresponding one of the at least one lower paddle, and an upper through hole of a corresponding one of the at least one upper paddle is opposite directly to the lower through hole; reversely rotating the at least one middle paddle by the stirring lever, separating the at least one middle paddle from the at least one upper paddle and the at least one lower paddle, such that the lateral flow strip falls into the test tube through the upper through hole; observing a detection result of the lateral flow strip.

Compared with the prior art, the present disclosure has the following technical effects.

In the present disclosure, sample tube(s) and test tube(s) are provided, and the sample tube(s) can be used for constant temperature reaction. After the constant temperature reaction, the lateral flow strip in each test tube can fall into a corresponding sample tube by rotating the middle paddle(s), without using the dropper to transfer the sample solution for detection. In this way, the constant temperature reaction of the sample solution may be combined with the reaction in the detection of the lateral flow strip(s), which not only makes the integration of the detection device higher, but also makes the detection process simpler and greatly improves the detection efficiency.

In the present disclosure, the lateral flow strip(s) is placed respectively in the test tube(s) to wait for detection, so that the lateral flow strip(s) can be prevented from being polluted by the external environment in the detection process, and thus the detection accuracy is ensured.

In the present disclosure, a plurality of paddles may be provided, so as to realize the simultaneous detection of a plurality of groups of different samples or the simultaneous detection of a plurality of groups of parallel experiments of the same sample. So, the parallelism and stability of test results are improved, and the detection efficiency is also greatly improved.

BRIEF DESCRIPTION OF THE DRAWINGS

In order to explain the embodiments of the present disclosure or the technical scheme in the prior art more clearly, the drawings needed in the embodiments will be briefly introduced below. Obviously, the drawings in the following description are only some embodiments of the present disclosure. For those skilled in the art, other drawings can be obtained according to these drawings without paying creative labor.

In the figures, 1. upper rotor; 2. middle rotor; 3. lower rotor; 4. upper paddle; 5. middle paddle; 6. lower paddle; 7. upper through hole; 8. test tube; 9. lower through hole; 10. sample tube; 11. middle stirring block; 12. upper groove; 13. upward stirring block; 14. middle groove; 15. lower groove; 16. water tank; 17. support column; 18. fastener; 19. stirring lever.

DETAILED DESCRIPTION OF THE PREFERRED EMBODIMENTS

The technical scheme in the embodiments of the present disclosure will be described clearly and completely with reference to the drawings in the embodiments of the present disclosure. Obviously, the described embodiments are only some embodiments of the present disclosure, rather than all the embodiments. Based on the embodiments of the present disclosure, all other embodiments obtained by those skilled in the art without paying creative labor belong to the scope of protection of the present disclosure.

The purpose of the present disclosure is to provide a detection device using a lateral flow strip for detection and a detection method thereof, so as to solve the problems existing in the prior art, improve the integration level of the detection device and improve the detection efficiency at the same time.

In order to make the above objects, features and advantages of the present disclosure more obvious and understandable, the present disclosure will be further explained in detail hereinafter with reference to the drawings and specific embodiments.

Embodiment 1

Figure 1:
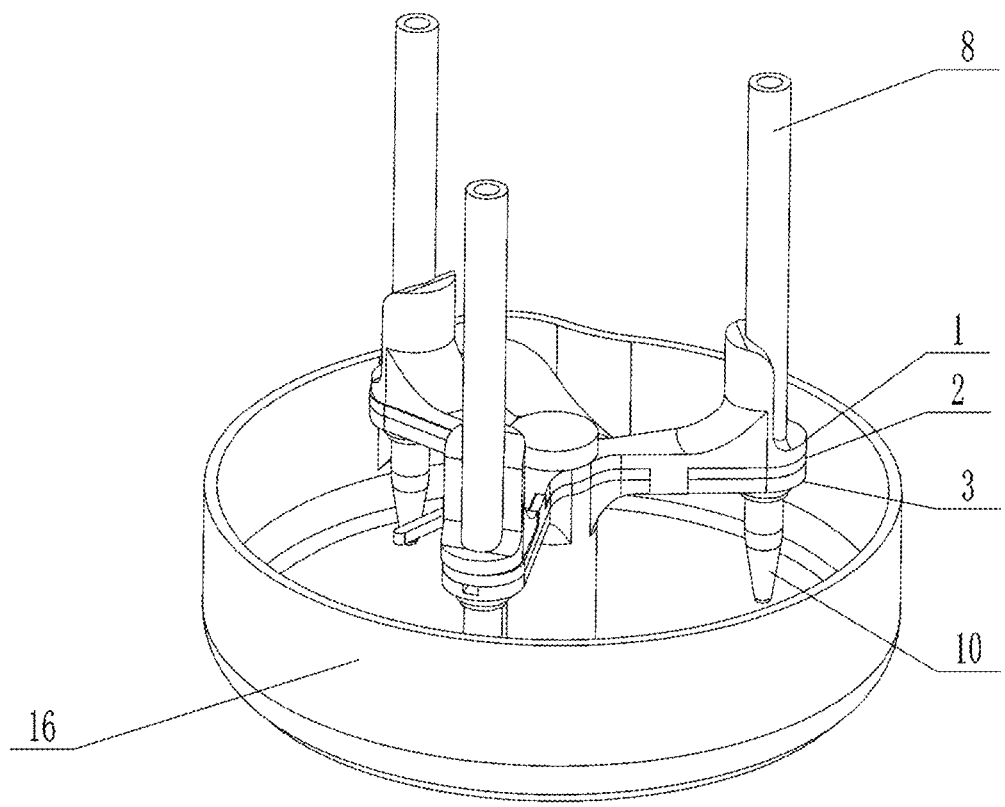
FIG. 1 is a schematic diagram of an overall structure according to an embodiment of the present disclosure.
Figure 2:
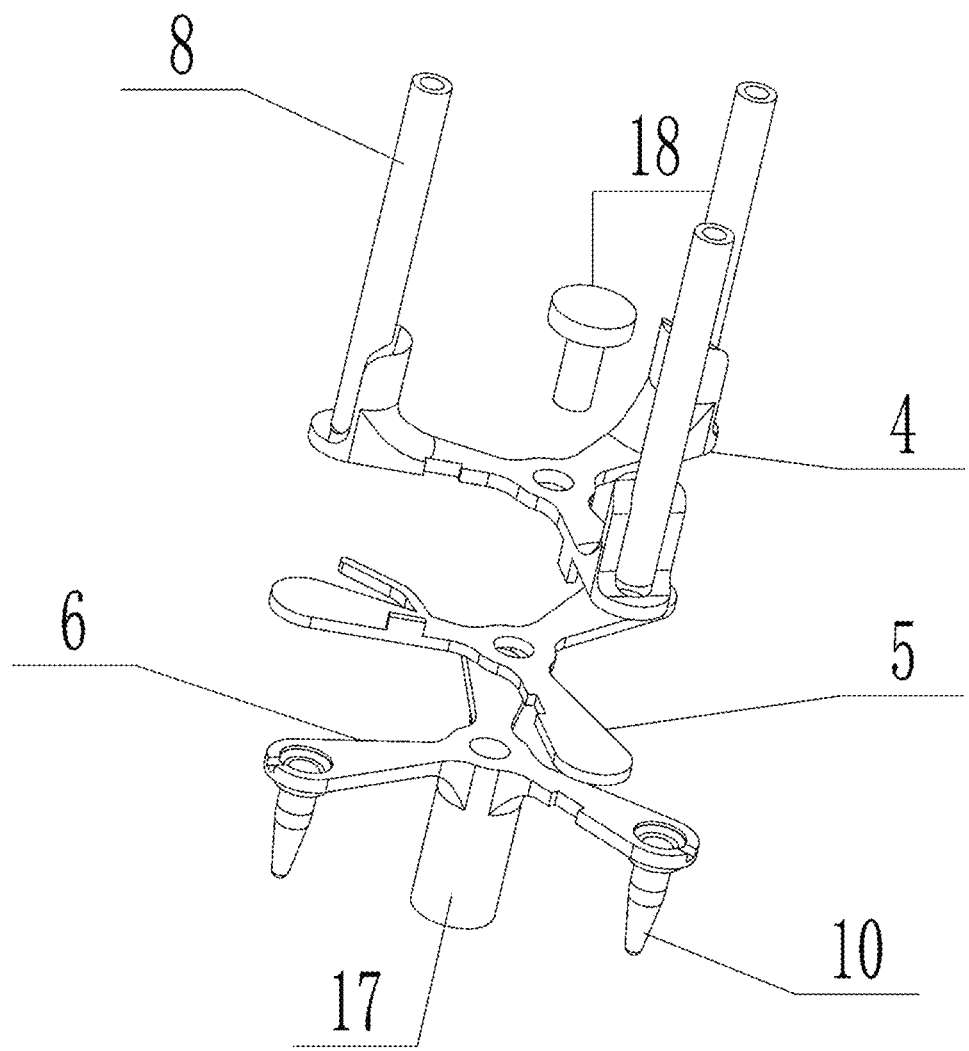
FIG. 2 is an exploded diagram of a structure that excludes a water tank according to an embodiment of the present disclosure.
Figure 3:
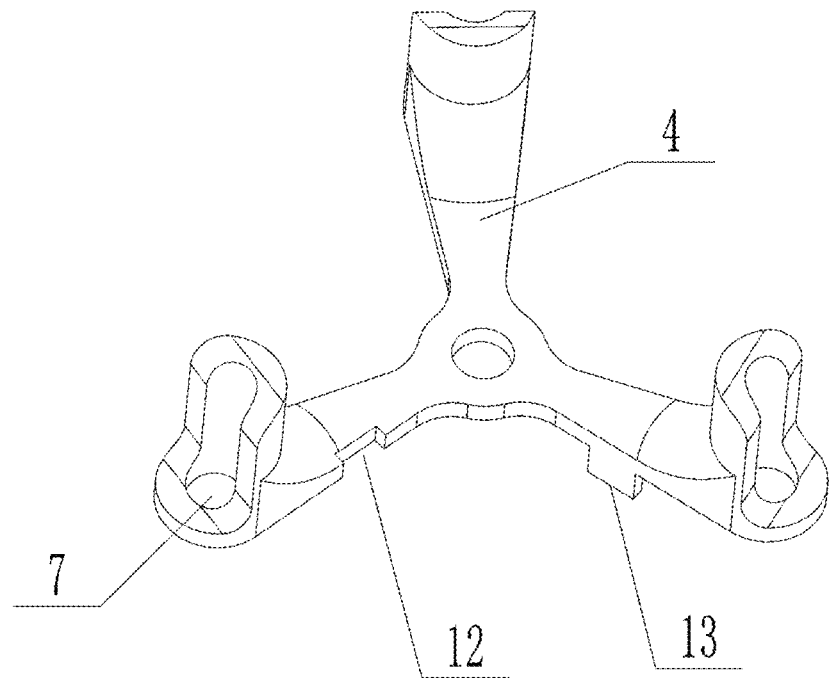
FIG. 3 is a schematic structural diagram of an upper rotor according to an embodiment of the present disclosure.
Figure 4:
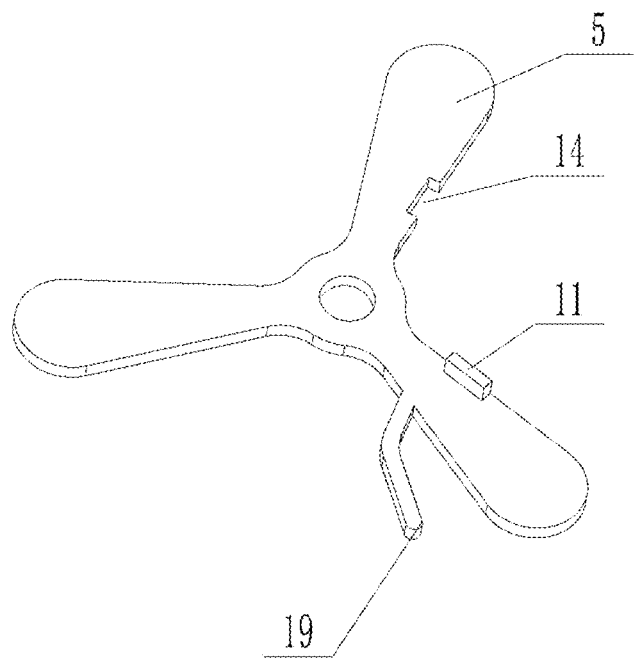
FIG. 4 is a schematic structural diagram of a middle rotor according to an embodiment of the present disclosure.
Figure 5:
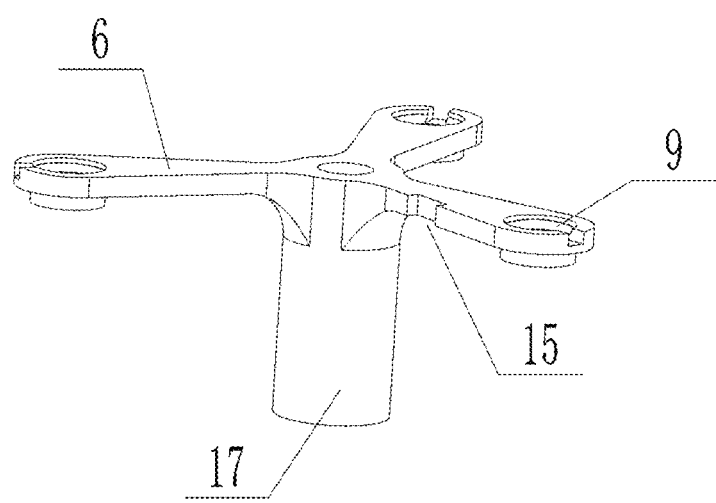
FIG. 5 is a schematic structural diagram of a lower rotor according to an embodiment of the present disclosure.

As shown in FIG. 1 to FIG. 5, a detection device using a lateral flow strip for detection is provided, which includes an upper rotor 1, a middle rotor 2 and a lower rotor 3 from top to bottom which are coaxial and rotatable relatively. The upper rotor 1, the middle rotor 2 and the lower rotor 3 are respectively provided with at least one upper paddle 4, at least one middle paddle 5 and at least one lower paddle 6 along respective circumferential directions. Each of the at least one upper paddle 4 is provided with a test tube 8 with openings at two ends thereof, and the test tube is configured for placing the lateral flow strip. A bottom opening of the test tube 8 is used for enabling the lateral flow strip 8 to fall out of the test tube 8. The middle paddle 5 blocks the bottom opening of the test tube 8. The lower paddle 6 is provided with a sample tube 10 for placing sample solution. The bottom opening of the test tube 8 is opposite to a top opening of the sample tube 10 up and down.

During detection, lateral flow strip(s) is added into the test tube(s) 8, respectively; then, the middle rotor 2 and the upper rotor 1 are rotated to expose the top opening(s) of the sample tube(s) 10. Sample solution is added into the sample tube(s) 10, and the middle rotor 2 and the upper rotor 1 are rotated above the lower rotor 3 to cover the top opening(s) of the sample tube(s) 10; then, the sample solution is heated. The usual heating method is a method of heating in a water bath manner. After heating for a certain time, the middle rotor and the upper rotor 1 are rotated; running buffer solution is added into the sample tube(s) 10; the middle rotor 2 and the upper rotor 1 are then rotated back; and then the middle rotor 2 is rotated independently again. Therefore, the bottom opening of each of the test tube(s) 8 is opposite directly to the top opening of the corresponding sample tube 10, and the lateral flow strip(s) falls into the sample tube(s) 10 respectively, so as to measure the sample solution.

In the embodiment, sample tubes 10 and test tubes 8 are provided. Those skilled in the art can use the sample tubes 10 to carry out constant temperature reaction. After the constant temperature reaction, the lateral flow strips in the test tubes 8 can fall into the respective sample tubes 10 by rotating the middle paddles 5, without using the dropper to transfer the sample solution for detection. In this way, the constant temperature reaction of the sample solution is combined with the reaction in the detection of the lateral flow strips, which not only makes the integration of the detection device higher, but also makes the detection process simpler and greatly improves the detection efficiency. At the same time, the lateral flow strips are placed in the respective test tubes 8 to wait for detection, so that the lateral flow strips can be prevented from being polluted by the external environment in the detection process, and the detection accuracy is ensured.

In this embodiment, the upper paddles 4, the middle paddles 5 and the lower paddles 6 are stacked. Each upper paddle 4 is provided with an upper through hole 7. A bottom end of the test tube 8 is fixed at the upper through hole 7. Each lower paddle 6 is provided with a lower through hole 9. A top of the sample tube 10 is fixed at the lower through hole 9. The upper through hole 7 and the lower through hole 9 are directly opposite to each other up and down. Therefore, the whole device is more compact.

In order to facilitate the synchronous rotation of the middle paddles 5 and the upper paddles 4, in this embodiment, one of the middle paddle 5 is provided with a middle stirring block 11 for stirring the upper paddles 4 to rotate synchronously and unidirectionally during rotation. The middle stirring block 11 can be provided on an upper surface of the middle paddle 5. Preferably, an outer side wall of the middle stirring block 11 is coplanar with a side wall of the middle paddle 5. Correspondingly, another one of the upper paddle 4 is provided with an upper groove 12 matched with the middle stirring block 11, so that the middle stirring block 11 can be embedded in the upper groove during rotation. A cross-sectional area of the upper groove 12 is the same as that of the middle stirring block 11. When the middle stirring block 11 is completely placed in the upper groove 12, the upper paddle 4 and the middle paddle 5 are opposite directly up and down. Therefore, the middle stirring block 11 can only drive the upper paddles 4 to rotate synchronously in one direction. When the middle stirring block 11 rotates reversely, the middle paddles can only rotate by itself, whereas the upper paddles 4 do not move. In this way, it may realize such a technical effect that: the middle paddles 5 can drive the upper paddles 4 to rotate synchronously in one direction to ensure that the lateral flow strips are always kept in the respective test tubes 8; and the middle paddles 5 may be separated from a location between the upper paddles 4 and the lower paddles 6, so that the lateral flow strips may automatically fall into the respective sample tubes 10.

In order to apply force to the middle paddles 5 to stir the middle paddles 5 to rotate, in this embodiment, one of the middle paddles 5 is further provided with a stirring lever 19 for stirring the middle paddles 5 to rotate. The stirring lever 19 can be located at any position on a side wall of the middle paddle 5. Preferably, the middle stirring block 11 and the stirring lever 19 are located at two sides of the middle paddle 5, respectively; and the two sides are in a horizontal direction of the middle paddle 5.

Further, in this embodiment, one of the upper paddles 4 is provided with an upper stirring block 13 for stirring the middle paddles 5 to rotate synchronously in one direction during rotation. The upper stirring block 13 is located at one side of the upper paddle 4; and the one side is in a horizontal direction of the upper paddle 4. The upper stirring block 13 is at a different side from the middle stirring block 11. A bottom end of the upper stirring block 13 is lower than a lower surface of the middle paddle 5. In addition, an outer side wall of the upper stirring block 13 is coplanar with a side wall of the upper paddle 4. Correspondingly, the middle paddle 5 and the lower paddle 6 are provided with a middle groove 14 and a lower groove 15 respectively. Cross-section areas of both the middle groove 14 and the lower groove 15 are the same as that of the upper stirring block 13. After the upper paddles 4 and the middle paddles 5 are rotated forward and further away from the lower paddles 6, the upper paddles 4 rotates reversely to drive the middle paddles 5 to be re-located above the lower paddles 6. Since the bottom end of the upper stirring block 13 is lower than the lower surface of the middle paddle 5, the upper stirring block 13 can interfere in the lower paddles 6 during reverse rotation, and the upper paddles 4 and the middle paddles 5 are rotated to be in place, so that the upper through holes 7 are directly opposite to the respective lower through holes 9.

Preferably, the lower through hole 9 is further provided with a vent hole for circulating air inside and outside the sample tube 10.

Further, in this embodiment, cross-sectional shapes of the upper paddle 4, the middle paddle 5, and the lower paddle 6 are the same. The upper paddles 4, the middle paddles 5, and the lower paddles 6 are each provided with three paddles. The simultaneous detection of a plurality of groups of sample solution or the simultaneous detection of a plurality of parallel samples of the same sample solution may be realized, thereby further improving the detection efficiency as well as the parallelism and stability of detection.

This embodiment further includes a water tank 16 for heating the sample tubes 10 in a water bath manner. A middle of the water tank 16 is provided with a support column 17. The upper rotor 1, the middle rotor 2 and the lower rotor 3 are all fixed on the support column 17 by a fastener 18. The sample tubes 10 are located in the water tank 16. The support column 17 can be integrally formed with the lower rotor 3, so that the lower rotor 3 is always immovable.

Embodiment 2

A detection method using a lateral flow strip for detection, the detection method is carried out by a detection device including at least one upper paddle, at least one middle paddle and at least one lower paddle, and the detection method includes the following steps.

In step 1), the at least one upper paddle, the at least one middle paddle and the at least one lower paddle are stacked and aligned, and the lateral flow strip is placed in a test tube on each of the at least one upper paddle.

In step 2), the at least one middle paddle is stirred to rotate forward through a stirring lever of the at least one middle paddle, the at least one upper paddle is enabled to rotate synchronously under driving of a middle stirring block of the at least one middle paddle, a lower through hole of each of the at least one lower paddle is exposed after the at least one middle paddle rotates, and sample solution is added into at least one sample tube on the at least one lower paddle; the at least one upper paddle is stirred reversely after the sample solution is added, and the at least one middle paddle is enabled to rotate synchronously under driving of an upper stirring block of the at least one upper paddle, so that each of the at least one middle paddle is re-located above a corresponding one of the at least one lower paddle.

In step 3), warm water at a predetermined temperature is added into a water tank of the detection device to heat the sample solution in a water bath manner, where the warm water has a higher liquid level than the sample solution.

In step 4), the at least one middle paddle is rotated forward after heating for predetermined time, and running buffer solution is added to the at least one sample tube.

In step 5), the at least one upper paddle is reversely rotated, so that each of the at least one middle paddle is located right above a corresponding one of the at least one lower paddle, and an upper through hole of a corresponding one of the at least one upper paddle is opposite directly to the lower through hole.

In step 6), the at least one middle paddle is reversely rotated by the stirring lever, the at least one middle paddle is separated from the at least one upper paddle and the at least one lower paddle, so that the lateral flow strip falls into the test tube through the upper through hole.

In step 7), a detection result of the lateral flow strip is observed.

Adaptability changes according to actual requirements fall within the protection scope of the present disclosure.

It should be noted that it is obvious to those skilled in the art that the present disclosure is not limited to the details of the above exemplary embodiments, and that the present disclosure can be realized in other specific forms without departing from the spirit or basic characteristics of the present disclosure. Therefore, the embodiments should be regarded as exemplary and non-limiting from any point of view, and the scope of the present disclosure is defined by the appended claims rather than the above description, so it is intended to embrace all changes falling within the meaning and range of equivalent elements of the claims in the present disclosure. Any reference numerals in the claims should not be regarded as limiting the claims involved.

What is claimed is:

1. A detection device using a lateral flow strip for detection, the detection device comprising an upper rotor, a middle rotor and a lower rotor from top to bottom which are coaxial and rotatable relatively, wherein the upper rotor, the middle rotor and the lower rotor are respectively provided with at least one upper paddle, at least one middle paddle and at least one lower paddle along respective circumferential directions; each of the at least one upper paddle is provided with a test tube with openings at two ends thereof, and the test tube is configured for placing the lateral flow strip; a bottom one of the openings of the test tube is used for enabling the lateral flow strip to fall out of the test tube; a corresponding one of the at least one middle paddle blocks the bottom one of the openings of the test tube; the at least one lower paddle is provided with at least one sample tube for receiving a sample solution; and the bottom one of the openings of the test tube is opposite to a top opening of a corresponding one of the at least one sample tube up and down.

2. The detection device according to claim 1, wherein the at least one middle paddle is provided with a middle stirring block for stirring the at least one upper paddle to rotate synchronously and unidirectionally.

3. The detection device according to claim 2, wherein the at least one middle paddle is further provided with a stirring lever for applying force to stir the at least one middle paddle to rotate.

4. The detection device according to claim 3, wherein the middle stirring block and the stirring lever are located at two sides of a same middle paddle of the at least one middle paddle respectively, and the two sides are in a horizontal direction of the same middle paddle.

5. The detection device according to claim 4, wherein one upper paddle of the at least one upper paddle is provided with an upper stirring block for stirring the at least one middle paddle to rotate synchronously and unidirectionally, and the upper stirring block is located at one side of the one upper paddle, the one side is in a horizontal direction of the one upper paddle, and the upper stirring block and the middle stirring block are at different sides.

6. The detection device according to claim 5, wherein a bottom end of the upper stirring block is lower than a lower surface of a corresponding one of the at least one middle paddle.

7. The detection device according to claim 1, wherein the at least one upper paddle, the at least one middle paddle and the at least one lower paddle are stacked, each of the at least one upper paddle is provided with an upper through hole, a bottom end of the test tube is fixed at the upper through hole, each of the at least one lower paddle is provided with a lower through hole, a top of a corresponding one of the at least one sample tube is fixed at the lower through hole, the upper through hole and the lower through hole are directly opposite to each other up and down.

8. The detection device according to claim 2, wherein the at least one upper paddle, the at least one middle paddle and the at least one lower paddle are stacked, each of the at least one upper paddle is provided with an upper through hole, a bottom end of the test tube is fixed at the upper through hole, each of the at least one lower paddle is provided with a lower through hole, a top of a corresponding one of the at least one sample tube is fixed at the lower through hole, the upper through hole and the lower through hole are directly opposite to each other up and down.

9. The detection device according to claim 3, wherein the at least one upper paddle, the at least one middle paddle and the at least one lower paddle are stacked, each of the at least one upper paddle is provided with an upper through hole, a bottom end of the test tube is fixed at the upper through hole, each of the at least one lower paddle is provided with a lower through hole, a top of a corresponding one of the at least one sample tube is fixed at the lower through hole, the upper through hole and the lower through hole are directly opposite to each other up and down.

10. The detection device according to claim 4, wherein the at least one upper paddle, the at least one middle paddle and the at least one lower paddle are stacked, each of the at least one upper paddle is provided with an upper through hole, a bottom end of the test tube is fixed at the upper through hole, each of the at least one lower paddle is provided with a lower through hole, a top of a corresponding one of the at least one sample tube is fixed at the lower through hole, the upper through hole and the lower through hole are directly opposite to each other up and down.

11. The detection device according to claim 5, wherein the at least one upper paddle, the at least one middle paddle and the at least one lower paddle are stacked, each of the at least one upper paddle is provided with an upper through hole, a bottom end of the test tube is fixed at the upper through hole, each of the at least one lower paddle is provided with a lower through hole, a top of a corresponding one of the at least one sample tube is fixed at the lower through hole, the upper through hole and the lower through hole are directly opposite to each other up and down.

12. The detection device according to claim 6, wherein the at least one upper paddle, the at least one middle paddle and the at least one lower paddle are stacked, each of the at least one upper paddle is provided with an upper through hole, a bottom end of the test tube is fixed at the upper through hole, each of the at least one lower paddle is provided with a lower through hole, a top of a corresponding one of the at least one sample tube is fixed at the lower through hole, the upper through hole and the lower through hole are directly opposite to each other up and down.

13. The detection device according to claim 7, wherein the at least one upper paddle, the at least one middle paddle and the at least one lower paddle have same cross-sectional shapes, and are each provided with three paddles.

14. The detection device according to claim 7, wherein the detection device further comprises a water tank for heating the at least one sample tube in a water bath manner, a support column is fixed in the water tank, the upper rotor, the middle rotor and the lower rotor are all fixed on the support column, and the at least one sample tube is located in the water tank.

15. A detection method using a lateral flow strip for detection, the detection method being carried out by a detection device comprising at least one upper paddle, at least one middle paddle and at least one lower paddle; the detection method comprising:

stacking and aligning the at least one upper paddle, the at least one middle paddle and the at least one lower paddle, and placing the lateral flow strip in a test tube on each of the at least one upper paddle;

stirring the at least one middle paddle to rotate forward through a stirring lever of the at least one middle paddle, enabling the at least one upper paddle to rotate synchronously under driving of a middle stirring block of the at least one middle paddle, exposing a lower through hole of each of the at least one lower paddle after the at least one middle paddle rotates, and adding sample solution into at least one sample tube on the at least one lower paddle; stirring the at least one upper paddle reversely after the sample solution is added, and enabling the at least one middle paddle to rotate synchronously under driving of an upper stirring block of the at least one upper paddle, such that each of the at least one middle paddle is re-located above a corresponding one of the at least one lower paddle;

adding warm water at a predetermined temperature into a water tank of the detection device to heat the sample solution in a water bath manner, wherein the warm water has a higher liquid level than the sample solution;

rotating the at least one middle paddle forward after heating for predetermined time, and adding running buffer solution to the at least one sample tube;

reversely rotating the at least one upper paddle, such that each of the at least one middle paddle is located right above a corresponding one of the at least one lower paddle, and an upper through hole of a corresponding one of the at least one upper paddle is opposite directly to the lower through hole;

reversely rotating the at least one middle paddle by the stirring lever, separating the at least one middle paddle from the at least one upper paddle and the at least one lower paddle, such that the lateral flow strip falls into the test tube through the upper through hole; and observing a detection result of the lateral flow strip.

\* \* \* \* \*